United States Patent [19]

Stalcup et al.

[11] Patent Number: 5,016,651

[45] Date of Patent: May 21, 1991

[54] METHOD OF PROVIDING TOPOICAL ANESTHETIC IN A SANITARY AND CONVENIENT MANNER

[76] Inventors: Robert W. Stalcup, 21152 Pepopertree La., Mission Viejo, Calif. 92691; Robert G. McCall, 7468 E. Raintree Ct., Scottsdale, Ariz. 85258

[21] Appl. No.: 400,281

[22] Filed: Aug. 29, 1989

[51] Int. Cl.$^5$ .............................................. A61B 19/00
[52] U.S. Cl. ........................................ 128/898; 604/2
[58] Field of Search ....................... 206/438, 63.5, 443; 604/1-3; 128/898

[56] References Cited

U.S. PATENT DOCUMENTS

| | | | |
|---|---|---|---|
| 3,078,856 | 2/1963 | Bender et al. | 132/321 |
| 3,228,398 | 3/1963 | Leonard et al. | 604/1 |
| 4,194,290 | 3/1980 | Vallhonrat | 433/141 |
| 4,397,395 | 8/1983 | McKelvey | 206/369 X |
| 4,401,130 | 8/1983 | Halford et al. | 604/1 |
| 4,448,307 | 5/1984 | Roggenkamp | 206/369 |
| 4,887,994 | 12/1989 | Bedford | 604/2 X |

OTHER PUBLICATIONS

Webster's Third World Dictionary, G. L. C. Merriam Company, Springfield, MA, 1966.

*Primary Examiner*—C. Fred Rosenbaum
*Assistant Examiner*—Corrine Maglione
*Attorney, Agent, or Firm*—Knobbe, Martens, Olson & Bear

[57] ABSTRACT

An improved applicator for applying a topical anesthetic to a patient's mucosal tissue is disclosed, and includes a sponge-like dispenser member characterized by a relatively large surface area. The dispenser member is attached to an elongated handle. A predetermined quantity of the topical anesthetic is preapplied to the applicator member. A number of the applicators are stored in a refillable dispenser apparatus, wherein a refill dispsenser housing defines a number of applicator wells, each for receiving one of the applicators. The handles of the applicators can be color coded to indicate the flavor of the topical anesthetic which has been preapplied to the applicator.

4 Claims, 1 Drawing Sheet

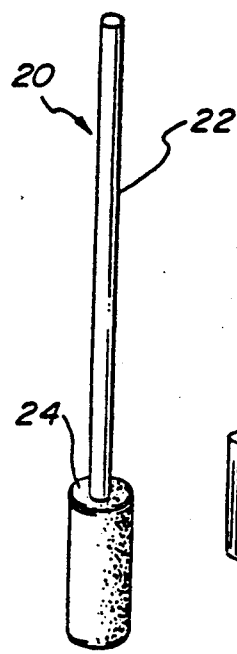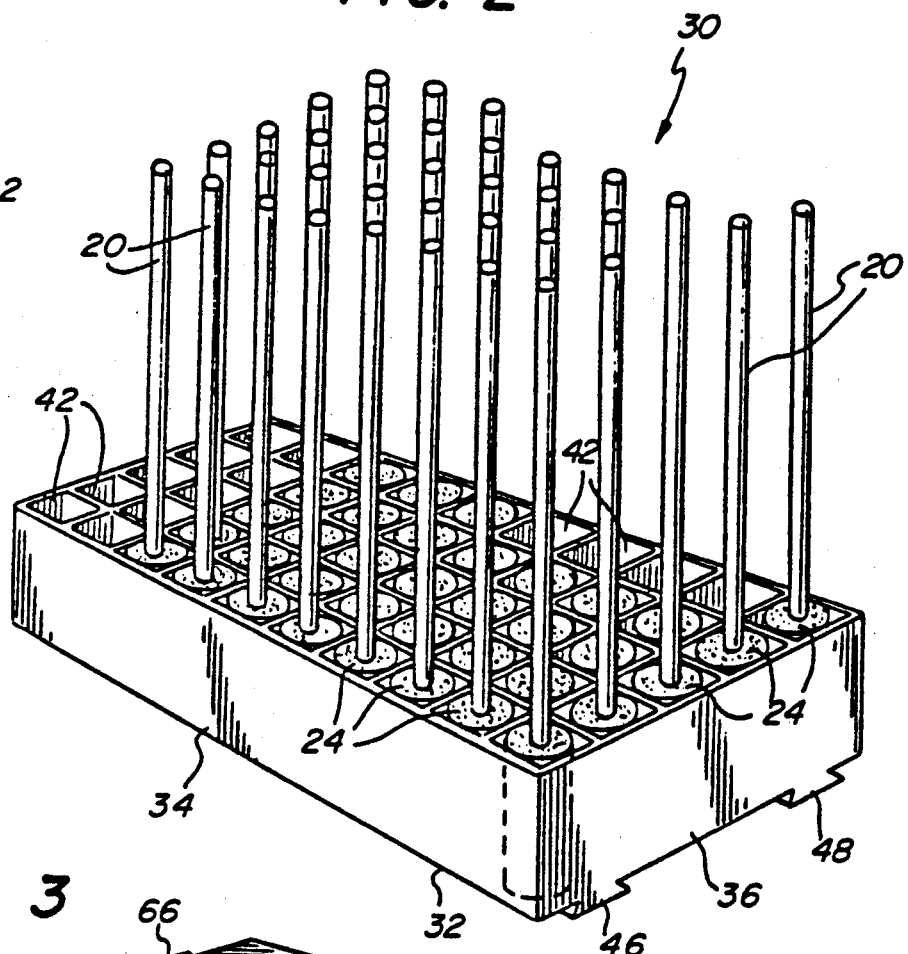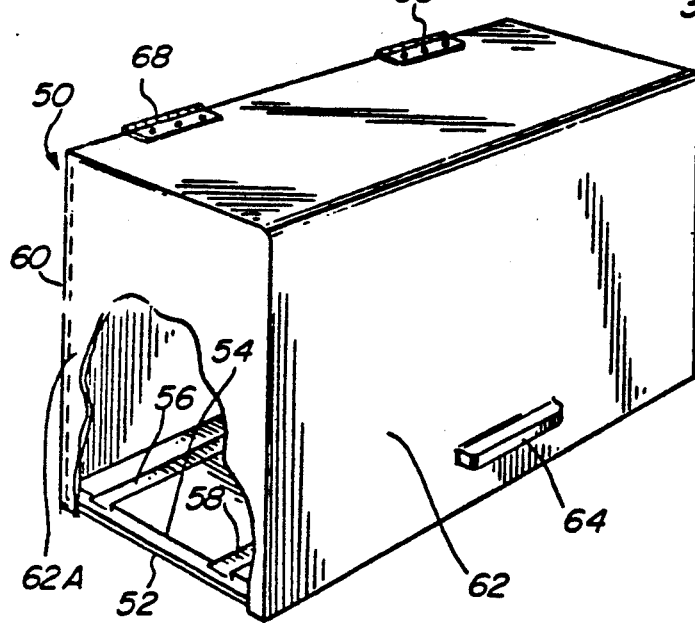

METHOD OF PROVIDING TOPOICAL ANESTHETIC IN A SANITARY AND CONVENIENT MANNER

BACKGROUND OF THE APPLICATION

The present invention relates to applicators for applying topical anesthetics to a patient's mucosal tissue, such as the patient's mouth for locally anesthetizing the patient's mucosal tissue.

Topical anesthetics are in common use today to locally anesthetize an area of a patient's mouth prior to carrying out a particular dental procedure, such as a blockage injection. Commonly used topical anesthetics include derivatives of benzocaine (ethyl aminobenzoate) or zylocaine (lidocaine) in a non-irritating water soluble base composed of polymerized polyethylene gylcols.

The anesthetic is typically supplied in small jars containing a quantity of anesthetic sufficient for a number of dental procedures. Conventionally the dentist applies the topical anesthetic by first dipping a cotton swab into the anesthetic in the jar to apply a quantity of the anesthetic to the swab, with the swab then used to transfer the anesthetic to the localized area of the patient's mouth. The same jar is typically a "community" jar used for a number of procedures for different patients. Alternatively, small multiple dose syringes filled with the anesthetic have been used to dispense the anesthetic to cotton rolls and swabs.

The conventional system for applying topical anesthetic suffers several disadvantages. The dentist or dental assistant must individually precoat the swab by dipping it into the community jar. This is time consuming, and it is difficult to apply a precise or desired quantity of the topical anesthetic. Sometimes too much anesthetic is applied to the cotton swab and the anesthetic can drip off, e.g., onto the patient's tongue or throat. The dripping can cause discomfort to the patient or anesthesize the wrong area. The use of a community jar may lead to unsanitary conditions if the jar is not sealed after each use. A cotton swab has a relatively small surface area, and therefore a second application may be required for some procedures.

SUMMARY OF THE INVENTION

It is therefore an object of the invention to provide an improved, single-use applicator for topical anesthetics to which has been preapplied a predetermined quantity of the topical anesthetic, and providing an increased surface area of contact with the mucosal tissue, enhancing the effect of the anesthetic.

It is a further object of the invention to provide a dispenser system for the improved applicator to provide pre-coated applicators in a sanitary and convenient manner.

These and other objects and advantages are achieved by a topical anesthetic applicator and dispenser system in accordance with the invention. The applicator comprises a sponge-like applicator member characterized by a relatively large surface area and high absorption of the topical anesthetic, and an elongated handle affixed to the sponge-like applicator member. A predetermined amount of topical anesthetic is preapplied to the applicator member in accordance with the invention. The relatively large surface area of the applicator member enhances the effect of the anesthetic to the mucosal tissue.

The applicators are preferably dispensed from a dispenser apparatus comprising a refill dispenser defining a plurality of applicator wells, each for receiving one of the applicator members. The refill dispenser housing is removably received within a dispenser base structure which includes a lid which can be raised or lowered, the lid covering the wells when in the lowered position. Preferably the refill dispenser includes a large number of wells, thereby holding a large number of applicators. The handles of the applicators may be color coded to indicate the flavor of the anesthetic.

BRIEF DESCRIPTION OF THE DRAWINGS

These and other features and advantages of the present invention will become more apparent from the following detailed description of an exemplary embodiment thereof, as illustrated in the accompanying drawings, in which:

FIG. 1 is a perspective view of an improved applicator for topical anesthetics in accordance with the invention.

FIG. 2 is a perspective view of an applicator dispenser for holding a plurality of dispensers as shown in FIG. 1.

FIG. 3 is a perspective view of a dispenser base for receiving the dispenser of FIG. 2 to supply the applicators in a sanitary dispenser system.

DETAILED DESCRIPTION OF THE PREFERRED EMBODIMENTS

Referring now to FIG. 1, a preferred embodiment of the applicator 20 for topical anesthetics is illustrated. The preferred embodiment is discussed in the context of dental applications, although it is to be understood that the invention has utility generally to apply topical anesthetics to mucosal tissue. Thus, other medical applications exist to apply anesthetic to such exemplary areas as the mucosal tissue in the nose.

The applicator 20 comprises an elongated handle 22 covered at one end thereof by an applicator member 24 characterized by an extended surface area. Preferably the member 24 comprises a material such as a soft sponge-like material such as an open celled foam rubber or like material. One shape of the applicator member 24 suitable for this purpose is a cylindrical shape as shown in FIG. 1. Other shapes and configurations can also be employed. The cylindrical configuration is well suited to dental applications. This configuration facilitates the application of positive pressure of the applicator member 24 against the mucosal tissue, which is particularly useful to anesthetize a local area in preparation for a block injection. Obviously the material chosen for member 24 must be non-toxic, and is preferably absorbent of the particular topical anesthetic to be applied.

For dental applications, the overall length of the applicator 20 is preferably in the range of 3 to 4 inches with a handle diameter of about ⅛ inch; an overall length of about 3½ inches is particularly advantageous for dental applications. The member 24 preferably has an outer diameter of ¼ to ½ inch with a cylinder length in the range of ½ to ¾ inch. Handles and applicator members of other dimensions may also be used.

The soft sponge applicator member 24 serves to carry the topical anesthetic, and has the advantage of increasing the surface area of contact with the patient's mucosal tissue, as compared to the surface area of a conventional cotton swab, thereby enhancing the effect of the anesthetic. When an applicator member 24 is employed having the exemplary dimensions described above, it may be used to apply the anesthetic to a tissue surface area adjacent two or three teeth. In contrast, the conventional cotton swab typically covers only a surface area adjacent a single tooth, requiring two or more swab applications for some procedures. When the applicator 20 is used to locally anesthetize an area adjacent the upper teeth, for example, the diameter of the applicator 20 is sufficient to wedge the applicator 20 between the patient's cheek and jaw. Thus, the applicator remains in contact with the mucosal tissue without being held in place by the dentist or technician. When cotton swabs have been used for this purpose, the swabs have a tendency to fall out due to the relatively small diameter of the cotton swab.

In accordance with the invention, a predetermined amount of the topical anesthetic is applied to the applicator member 24. This may be done, e.g., by dipping the dispenser in a bath of the anesthetic. Other techniques may also be used to apply the anesthetic. Typically the anesthetic may be in a substantially liquid form when applied to the applicator member 24, and thereafter solidifies into a gel-like form on the applicator. The sponge-like material of member 24 absorbs the anesthetic at least into the cells at the surface of member 24. The "predetermined quantity" of the anesthetic applied to the applicator 20 will be determined by the absorptiveness of the sponge-like material and the viscosity of the anesthetic. The quantity may not be precisely determined, and it is not critical for dental applications that the quantity be precisely measured. It is desired that the applicators have about the same quantity of anesthetic applied to member 24, that enough anesthetic be applied to effectively treat mucosal tissue coming into contact with the surface area of member 24, and yet that an excessive amount not be applied such that the anesthetic drips from the applicator 20 when dispensed for use.

After a particular applicator 20 has been used once, it is discarded. This one time use without a community jar tends to increase patient confidence in the anesthetic procedure.

Referring now to FIG. 2, a perspective view of a refill dispenser 30 is disclosed for the applicators 20 illustrated in FIG. 1. The dispenser 30 comprises a box-like structure having a bottom plate 32 and four upright walls 34, 36, 38 and 40. The interior of the dispenser 30 is divided into a plurality of partitioned wells 42, each for receiving an applicator 20. The applicators 20 are preferably disposed with the applicator members 24 inserted in the wells 42 so that the handles 22 protrude for convenient access by the dentist. Preferably the refill dispenser 30 includes at least fifty wells 42.

The dispenser 30 may be fabricated from plastic or other similar material. Protruding tracks 46 and 48 having a wedge-shaped cross-sectional configuration are formed in the bottom surface 32 of the dispenser 30 and removably secure the dispenser 30 to the base member 50 shown in FIG. 3.

FIG. 3 illustrates the base structure 50 used to support the dispenser 30 and provide a closable top. The base 50 comprises a weighted base member 52 into which is fitted a plate 54 having defined therein base grooves 56 and 58 which mate with the tracks 46 and 48 formed in the bottom of the dispenser 30. The plate 54 supports the refill dispenser 30. The base 50 further comprises a back upright wall 60 and a curved top cover member 62, which is connected to the back wall 60 by hinges 66 and 68. The top member 62 further comprises side wall elements on either side of the curved top 62 (62A is shown in FIG. 3) to enclose the sides of the structure 50. A handle 64 is provided to facilitate raising and lowering the top 62. The base structure 50 and the refill dispenser 30 cooperate to define a sanitary enclosure for the applicators 20 which is conveniently accessible by the dentist.

The dispenser 30 can be slipped into the base structure 50 by raising the cover 62, aligning the tracks 46 and 48 of the dispenser 30 with the corresponding track grooves 56 and 58 of the base plate 54, and sliding the dispenser 30 into the base structure 30.

It is contemplated that the dispenser 30 will be marketed with all wells filled with the applicators as described above with respect to FIG. 1. The filled dispenser can be shipped in sealed packaging, and used to refill the base structure 50. Thus, no handling of the individual applicators need be made during shipping or installation of the dispenser 30 in the base structure 50.

It is known to use anesthetics having different taste flavors, e.g., strawberry, butterscotch and the like. In accordance with another aspect of the invention, the handles 22 can be color coded to indicate the particular flavor of the preapplied anesthetic. The dentist can then ask the patient which flavor is desired, and immediately pick up an applicator preapplied with the anesthetic of that flavor simply by knowing the particular color associated with the selected flavor. For convenience, each row of applicators 20 in the dispenser 30 may hold applicators of a particular flavor of anesthetic.

It is understood that the above-described embodiment is merely illustrative of the possible specific embodiments which may represent principles of the present invention. Other arrangements may readily be devised in accordance with these principles by those skilled in the art without departing from the scope of the invention.

What is claimed is:

1. A method of providing topical anesthetic in a sanitary and convenient manner for use on patients, said method for use with a base having a selectively openable cover, comprising the steps of:

providing a topical anesthetic suitable for use with mucosal tissue;

providing an applicator having an elongated handle and an applicator member mounted on one end of said elongated handle;

providing a dispenser for removably receiving said applicator, said dispenser being sized to allow insertion thereof into the base and so that the selectively openable cover of the base may close over said dispenser;

applying a predetermined amount of said anesthetic to said applicator member of said applicator; and placing said applicator within said dispenser so that said handle protrudes to facilitate removal of said applicator from said dispenser for use on patients.

2. The method of claim 1, further comprising the step of sealing said dispenser after said placing step to maintain said applicator in sanitary condition during shipping and installation of said dispenser in the base.

3. A method of providing topical anesthetic in a sanitary and convenient manner for use on patients, comprising the steps of:

providing a topical anesthetic suitable for use with mucosal tissue;

providing an applicator having an elongated handle and an applicator member mounted on one end of said elongated handle;

providing a dispenser for removably receiving said applicator;

providing a base having a selectively openable cover arranged so that said dispenser may be received in said base and so that said cover may be closed over said dispenser when so received;

applying a predetermined amount of said anesthetic to said applicator member of said applicator;

placing said applicator within said dispenser so that said handle protrudes to facilitate removal of said applicator from said dispenser;

placing said dispenser within said base; and closing said cover.

4. The method of claim 3, further comprising the step of sealing said dispenser after placing said applicator within said dispenser to maintain said applicator in sanitary condition until use.

* * * * *